United States Patent [19]
Florine et al.

[11] Patent Number: 5,102,870
[45] Date of Patent: Apr. 7, 1992

[54] TREATMENT AND PREVENTION OF ORAL MUCOSITIS WITH GROWTH FACTORS

[75] Inventors: Dagne L. Florine, Moraga, Calif.; Thomas J. Smith, Ashland, Va.

[73] Assignees: Schering AG, Berlin, Fed. Rep. of Germany; Virginia Commonwealth University, Richmond, Va.

[21] Appl. No.: 339,463

[22] Filed: Apr. 14, 1989

[51] Int. Cl.$^5$ .............................................. A61K 37/02
[52] U.S. Cl. ........................................ 514/12; 514/2; 514/21; 514/900; 514/902; 424/49
[58] Field of Search ............. 514/12, 21, 11, 900–902; 424/49

[56] References Cited

U.S. PATENT DOCUMENTS

| 4,749,683 | 6/1988 | Murphy et al. | 514/2 |
| 4,816,561 | 3/1989 | Todaro | 530/324 |
| 4,863,899 | 9/1989 | Todaro | 514/9 |
| 4,863,902 | 9/1989 | Amagase et al. | 514/12 |

FOREIGN PATENT DOCUMENTS

| 0161817 | 11/1985 | European Pat. Off. . |
| 0190018 | 8/1986 | European Pat. Off. . |
| 0261599 | 3/1988 | European Pat. Off. . |
| 84/01106 | 3/1984 | PCT Int'l Appl. . |
| 89/04664 | 6/1989 | PCT Int'l Appl. . |
| WP89/06139 | 7/1989 | PCT Int'l Appl. . |

OTHER PUBLICATIONS

Mandel, I. D., "The Functions of Saliva", J. Dent. Res., pp. 623–627, (Feb. 1987).
Peterson, D. E., et al., "Oral Complications of Cancer Chemotherpy: Present Status and Future Studies", Cancer Treatment Reports, (1982), 66(6): 1251–1255.
Duperon, D. F., "The Effect of Topical Leukovorin on the Gingiva of Long Evans Rats Undergoing Surgery", (1978), J. of Oral Medicine, 33(1): 12–16.
Steidler, N. E. et al., "Histomorphological Effects of Epidermal Growth Factor on Skin and Oral Mucosa in Neonatal Mice", Archs. Oral. Biol., (1980), 25: 37–43.
Gabilove, J. L. et al., "The Effect of G-CSF on Neutropenia and Associated Mobidity Due to Chemotherapy for Transitional-Cell Carcinoma of the Urothelium", New Eng. J. of Med., (1988), 318(22): 1414–1422.
Konturek, S. J. et al., "Role of EGF in Healing of Chronic Gastroduodenal Ulcers in Rats", Gastroenterology, (1988), 94: 1300–1307.
Todaro, G. J. et al, "TGFs: Properties & Possible Mechanisms of Action", J. of Supramolecular Structure & Cell. Biochem., (1981), 15: 287–301.
Derynck, R., "TGF-α: Structure & Biological Activities", J. of Cellular Biochemistry, (1986), 32: 293–304.
Konturek, S. J. et al., "Gastric Cytoprotection by EGF", Gastroenterology, (1981), 81(3): 438–443.
Niall, M. et al., "The Effect of EGF on Wound Healing in Mice", J. of Surgical Research, (1982), 33: 164–169.
Brown, G. L. et al., "Enhancement of Epidermal Regeneration by Biosynthetic EGF", J. Exp. Med., (1986), 163: 1319–1324.
Bright, R., "Combinations of Growth Factors: Periodontal Bone Regeneration & Other Applications", Abstract, Technology Management Group Conference, (1988).
Brightwell, J. R. et al., "Biosynthetic Human EGF Acceleration Healing of Neodecardron-Treated Primate Corneas", Inves. Opth. & Visual Sci., (1985), 26(1): 105–110.
Lawrence, W. T., et al., "The Reversal of an Adrianycin Induced Healing Impairment with Chemoattractants & Growth Factors", Ann. Surg., (1986), 203(2): 142–147.

(List continued on next page.)

*Primary Examiner*—F. T. Moezie
*Attorney, Agent, or Firm*—Shelley G. Precivale; Karen Babyak Dow

[57] ABSTRACT

Methods are provided of preventing and treating chemotherapy or radiotherapy induced oral mucositis in a mammal by administering an effective dose of a growth factor, such as TGF-α. The growth factor may be used alone or in combination with other growth factors. Typically the effective dose is within the range of about 0.01–100 µg/dose, administered 2–4 times daily.

10 Claims, 1 Drawing Sheet

OTHER PUBLICATIONS

Robinson, B. A., et al., "EGF Has No Effect on Murine Intestine Epithelial Damage & Regeneration After Melphalan", Br. J. Cancer, (1985), 52: 733-737.

Southgate, J. et al., "Primary Culture of Human Oral Epithelial Cells", Laboratory Investigation, (1987), 56(2): 211-223.

A. W. Burgess, "Epidermal Growth Factor and Transforming Growth Factor $\alpha$", British Medical Bulletin, 45(2): 404-424, (Apr. 1989).

E. Nexo and S. S. Poulsen, "Does Epidermal Growth Factor Play a Role in the Action of Sucralfate?", Scand. J. Gastroenterol. Suppl., 127: 45-49, (1987).

M. H. Bronchud and T. M. Dexter, "Clinical Use of Haematopoietic Growth Factors", Blood Reviews, 3(1): 66-70, (1989).

J. B. Epstein, "The Painful Mouth. Mucositis, Gingivitis, and Stomatitis", Infectious Syndromes of the Head and Neck, 2(1): 183-202, (1988).

TREATMENT AND PREVENTION OF ORAL MUCOSITIS WITH GROWTH FACTORS

BACKGROUND OF THE INVENTION

Oral mucositis is a common side-effect associated with cancer treatment, both with chemotherapy and radiotherapy. Mucositis accounts for significant pain and discomfort for these patients, and ranges in severity from redness and swelling to frank ulcerative lesions. Of primary concern are those patients undergoing: chemotherapy for cancer such as leukemia, breast cancer or as an adjuvant to tumor removal; radiotherapy for head and neck cancer; and combined chemotherapy and radiotherapy for bone marrow transplants. All bone marrow transplant and about half of the head and neck cancer patients develop mucositis (about 10,000 cases/yr and 15,000 cases/yr, respectively). Also, breast cancer patients contemplating extended 5-fluorouracil treatment (about 50,000 cases/yr) would be likely to develop mucositis from such therapy.

Chemotherapeutic agents and radiation can kill or damage the epithelial cells lining the oral cavity. Such damage includes the inhibitory effect that chemotherapeutic agents may have on mitoses of the rapidly dividing cells of the oral basal epithelium. Consequently, the renewal rate of the basal epithelium is reduced, which results in atropic changes of the mucosa and eventually ulceration. The severity of damage is related to the type and dose of chemotherapeutic agent(s) and concomitant therapy such as radiotherapy. Further, ulceration is hastened if sources of chronic irritation such as defective dental restorations, fractured teeth or ill-fitting dental prostheses are present.

Mucositis most often affects the nonkeratinized mucosa of the cheeks, lips, soft palate, ventral surface of the tongue and floor of the mouth, approximately one to two weeks after cancer therapy. The lesions often become secondarily infected and become much harder to heal. At present, there is no effective treatment for mucositis. Therapy is limited to pain medications and treatment of secondary infection. In particular, recommendations have included treatment with topical anesthetics such as xylocaine, benzocaine and cocaine, treatment with solutions which coat the ulcerative lesions with a polysaccharide gel and use of antiseptic solutions such as Chlorhexadine. While all these treatments do provide some relief, none are directed to the actual healing of oral mucositis, which entails directly healing the mucosal epithelium cells.

Treatment of chemotherapy or radiotherapy induced oral mucositis presents some very unique problems. As used herein the term "oral" is used to mean both the oral cavity and the esophagus. First, there is the nature of the mucosal surface itself. As used herein the term "oral mucosa" means the mucocutaneous junction of the lips to include the buccal and labial mucosa, the alveolar mucosa, the floor of the mouth, the dorsal and ventral surfaces of the tongue, the hard and soft palate, the posterior-oropharynx and the esophagus. The histologic architecture of the oral cavity mucosal surface is unique as it is comprised of mucosal squamous epithelium which does not undergo complete cornification. Thus, it is distinct from skin tissue which is cornified squamous epithelial but not mucosal in nature, and from gastric and intestinal tissue which is mucosal but is columnar rather than squamous epithelium. Second, there is the nature of the oral cavity. The mobility and physical action of the tongue markedly decrease the adhesion of any dressing containing a therapeutic agent to the oral cavity surface. The presence of teeth causes constant mucosal trauma. Further, the composition of the saliva is fairly complex, containing for example, numerous enzymes such as lysozyme, amylase and ligase, kallikrein, immunoglobulins, lubricatory molecules such as the parotid prolinerich glycoprotein-albumin complex, zinc-binding proteins such as gustin and mucin glycoproteins. Additionally, there is a unique and dynamic bacterial flora which is affected by the patient's immunologic status. Lastly, there is the physical barrier effect of mucus, which lines the oral mucosal surface and decreases the ability of therapeutic agents to penetrate the epithelial surface. The mucosal tissue and environment of the oral cavity is thus distinguishable from other epithelial surfaces.

This invention pertains to the prevention and treatment of oral mucositis with growth factors. The use epidermal of growth factor in wound healing has been studied extensively in the gastrointestinal tract, including gastic, duodenum, jejunum, ileium and colonic tissue. However, studies done on oral cavity epithelial tissue have been primarily limited to subcutaneous injections of epidermal growth factor to measure the effect on intact mucosa. Steidler et. al, Arch Oral Biol. (1980) 25:37–43. There have been no studies done on wound healing of oral mucosal tissue where the epithelial layer and underlying stromal tissue have been damaged or destroyed as a result of chemotherapy or radiotherapy. Intravenous infusion of granulocyte colony stimulating factor appears to reduce the incidence and severity of oral mucositis in cancer patients. Gabrilove, The New England Journal of Medicine (1988) 318(22):1414–1422. However, the mechanism is likely to be its effect on increasing peripheral white blood cells thereby reducing secondary infection, rather than via growth promoting effects on basal epithelial or stromal cells.

SUMMARY OF INVENTION

This invention pertains to a method and composition for the prophylactic and therapeutic use of growth factors in the treatment of lesions due to chemotherapy or radiotherapy induced oral mucositis so as to reduce, delay or block the onset of mucositis. Treatment may be topical or systemic and growth factors may be delivered alone, in combination with one or more other growth factors, or together with a therapeutic agent.

In particular, this invention pertains to the use of growth factors and their analogs which are biologically active peptides and cause cell proliferation. More specifically this invention uses growth factors which bind to epidermal growth factor receptors, said growth factors containing six essential cysteine residues with their spacing being in the pattern of -Cys-(AA)$_a$-Cys-(AA)$_b$-Cys-(AA)$_c$-Cys-AA-Cys-(AA)$_d$-Cys-wherein AA is an amino acid residue, a is 7, b is 4 or 5, c is 10 and d is 8.

Even more specifically, this invention pertains to the use of transforming growth factor-alpha (TGF-α) for the prevention and treatment of oral mucositis.

DETAILED DESCRIPTION OF THE INVENTION

Figure 1:
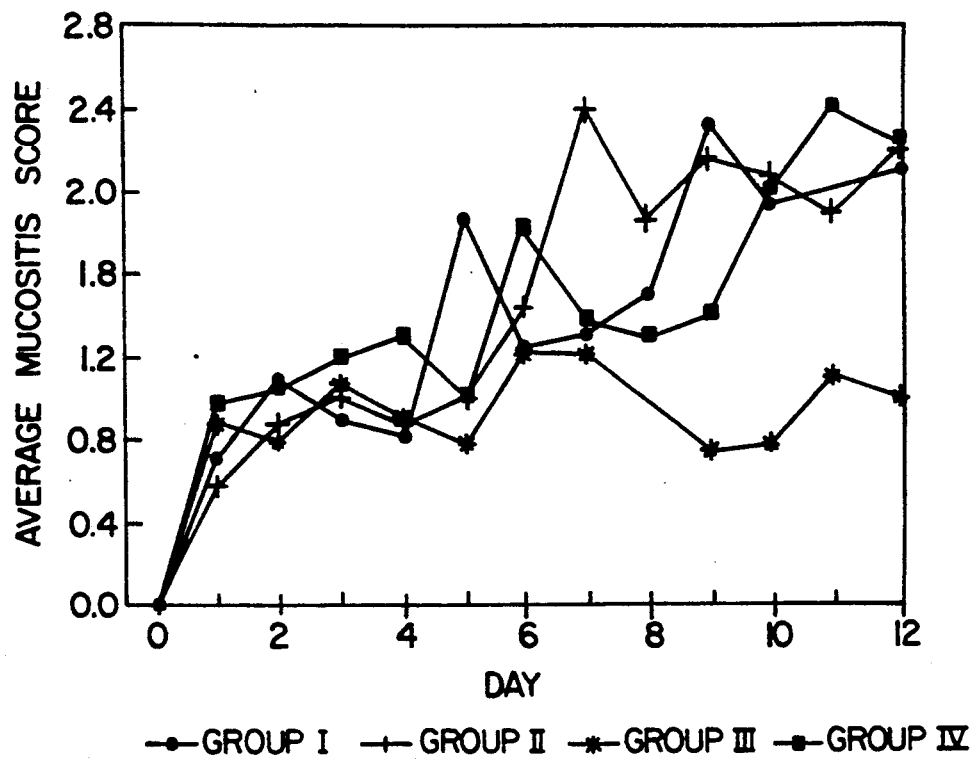
FIG. 1 illustrates the average oral mucositis scores (evaluating the extent of mucositis development) for control and TGF-α treated animals over a 12 day period.

This invention establishes that growth factors have the potential to rapidly accelerate the healing of chemotherapy and radiotherapy induced oral mucositis in mammals, particularly in the oral cavity. As used herein, the term "growth factor" means a biologically active polypeptide which causes cell proliferation, and includes both growth factors and their analogs. These include, without limitation, epidermal growth factor, transforming growth factors, nerve growth factor, acidic and basic fibroblast growth factor and angiogenesis factor, platelet-derived growth factor, insulin and insulin-like growth factors including somatomedins, myxoma and vaccinia virus-derived growth factors.

Accordingly, in one of its broadest aspects, the present invention is directed to all growth factors. Another aspect of the present invention is directed to growth factors which bind to epidermal growth factor receptors, said growth factors having a preferred molecular weight range of 5000–35,000 and having at least one peptide sequence having six essential residues in the spacing pattern of the formula I:

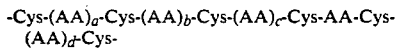
-Cys-(AA)$_a$-Cys-(AA)$_b$-Cys-(AA)$_c$-Cys-AA-Cys-(AA)$_d$-Cys-    I wherein AA is an amino acid residue selected from the group consisting of Val, Ser, His, Phe, Asn, Lys, Asp, Thr, Gln, Arg, Leu, Glu, Pro, Ala, Gly, Trp, Tyr, Ile and Met; and a is 7, b is 4 or 5, c is 10 and d is 8.

Another aspect of the invention is directed to those growth factors having the peptide sequence of the formula I, where b is 4. Still another aspect is directed to growth factors having the peptide sequence of the formula I, where b is 4 and AA is an amino acid residue selected from the group consisting of Val, Ser, His, Phe, Asn, Lys, Asp, Thr, Gln, Arg, Leu, Glu, Pro, Ala, Gly, Trp and Tyr.

Another aspect of the invention is directed to specific classes of growth factors having transforming growth factor properties which include polypeptide compounds of the formula II or oligomers thereof:

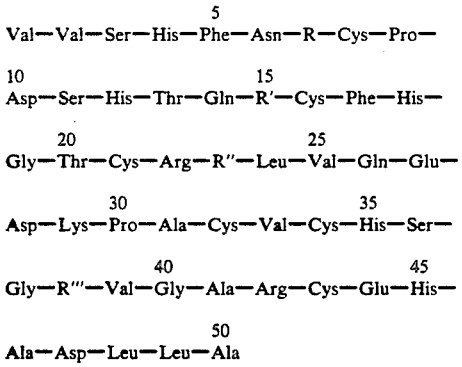

```
              5
Val—Val—Ser—His—Phe—Asn—R—Cys—Pro—

10                    15
Asp—Ser—His—Thr—Gln—R'—Cys—Phe—His—

20                25
Gly—Thr—Cys—Arg—R"—Leu—Val—Gln—Glu—

30                    35
Asp—Lys—Pro—Ala—Cys—Val—Cys—His—Ser—

40              45
Gly—R'''—Val—Gly—Ala—Arg—Cys—Glu—His—

50
Ala—Asp—Leu—Leu—Ala
```
                                        II wherein R is Asp or Lys, R' is Phe or Tyr, R" is Ser or Phe, and R''' is Phe or Tyr.

Still another aspect of the invention is directed to use of transforming growth factor-alpha (TGF-α) having the sequence of formula II where R is Asp, R' is Phe, R" is Phe, and R''' is Tyr. The TGF-α employed in the method and composition of this invention is a known compound disclosed in U.S. Pat. No. 4,816,561, the disclosure of which is incorporated herein by reference.

The growth factors can be administered therapeutically in an effective amount to treat existing lesions or they can be administered prophylactically, in an effective amount before onset of oral mucositis to either delay onset or prevent development of lesions altogether. The preferred use for this invention is prophylactic treatment. An effective dose is within the range of 0.01–100 μg/dose, preferably 0.1–50 μg/dose, said dose being administered 2–4 times daily.

This invention contemplates using growth factors both alone or in combination with other growth factors. Suitable combinations include, without limitation, epidermal growth factor and insulin-like growth factors, transforming growth factor—alpha and transforming growth factor—beta, and platelet—derived growth factor and insulin-like growth factors.

Use may be either systemic or topical, with the preferred embodiment being topical administration. The term "systemic" administration as used herein means administration of growth factors in a pharmaceutically acceptable non-toxic vehicle or carrier therefor, at some point distant from the wound site such that growth factors are delivered to the site via the blood stream. Systemic administration has the advantage of not having to overcome problems associated with the nature of the mucosal surface and the oral cavity. Growth factors can be used systemically in the form of a composition consisting of a growth factor together with any conventional pharmaceutically acceptable non-toxic vehicle or carrier suitable for parenteral administration such as normal saline, or a polymeric matrix material adapted to provide a slow release of the growth factor(s) to maintain suitable serum levels for prevention or treatment of mucositis. Compositions can be administered intravenously, intramuscularly or by percutaneous introduction in any other suitable manner.

The term "topical" as used herein, means administration of growth factors directly to the wound site. This can be accomplished in numerous ways. A liquid solution or suspension containing the growth factor(s) can be used in a manner similar to a mouthwash, where the liquid is swished around in the mouth so as to maximize treatment of lesions. Longer contact with the mucosal surface can be attained by selecting a suitable vehicle which is capable of coating mucosa. Typical examples are pectin containing formulations such as Orabase ® (Colgate-Hoyt Laboratories, Norwood, MA), sucralfate suspensions, Kaopectate and Milk of Magnesia. The formulation can also be a spreadable cream, gel, lotion or ointment having a pharmaceutically acceptable non-toxic vehicle or carrier. The growth factors of this invention can also be incorporated into a slow dissolving lozenge or troche, a chewing gum base, or a buccal or slow delivery prosthesis hooked onto a back molar, for example.

This invention also contemplates administering other therapeutic agents along with the growth factor(s). As the growth factor functions to promote healing of the lesions, therapeutic agents such as analgesics and anesthetics can be administered to alleviate the pain that accompanies oral mucositis. Additionally, therapeutic agents such as anti-infectivtes, anti-bacterials, anti-fungals and antiseptics can be administered to prevent or treat secondary infection of the lesions.

An animal model for studying the acute effects of chemotherapy and radiotherapy in the oral cavity was developed by Dr. Stephen T. Sonis at Brigham and Women's Hospital, Boston, Mass. This model was particularly suited for testing the efficacy of growth factors on chemotherapy mucositis. This model utilizes an acute regimen of 5-fluorouracil (5-FU) combined with mechanical irritation to induce mucositis. More specifically, intraperitoneal (i.p.) injections of 5-fluorouracil were combined with superficial mechanical mucosal irritation to result in clinical breakdown of the oral mucosa as characterized by ulcerative mucositis in Golden Syrian hamsters. Clinical and histologic evaluations had demonstrated that these changes were similar to those described in man and followed a pattern influenced by the degree of myelosuppression. For these reasons, it was believed that this model would be extremely beneficial in evaluating growth factors to treat mucositis.

The following experiment was performed to determine the effects of growth factors, specifically TGF-α, on the prevention and healing of mucositis induced by the administration of 5-FU in hamsters. Example 1:

Use of Growth Factors in Oral Mucositis

One hundred young male Golden Syrian hamsters were divided into four groups of 25 animals each. Beginning on day 0, animals received twice daily dosing of their cheek pouch buccal mucosa as follows:

| Group | Treatment |
|---|---|
| I | None |
| II | Orabase Only |
| III | TGF-α in Orabase (2 μg/dose) |
| IV | TGF-α in Orabase (20 μg/dose) |

Medication was applied in a volume of 0.2 ml of Orabase per cheek pouch. The right cheek pouch was mechanically irritated by superficial scratching starting at day 0, daily until erythematous changes were noted. For most animals, such changes were noted by day 2 and mechanical irritation discontinued. For the remaining animals, mechanical irritation was stopped at day 3. Beginning on day 0, all of the animals received i.p. injections of 5-FU at a dose of 60 mg/kg body weight, with additional dosing on days 5 and 10. The animals were observed and weighed daily. On days 2, 4, 6, 8, 10, 12, 14, 16, 18 and 20, two animals were randomly sacrificed in each group. Cheek pouches were biopsied. The tissue was then placed in 10% formalin for histologic study according to established methods, and subsequently stained with hematoxylin and eosin. The following parameters were evaluated and scored: inflammatory infiltrate, degree of epithelial atropy, extent of epithelial breakdown/ulceration, mitotic activity at would margins and evidence of superficial/secondary infection. Two randomly selected hamsters from each group had their cheek pouches photographed daily. The animals were weighed and observed daily. An average weight loss of 15-20% was observed for all groups. Mucositis was scored using the following established scale:

Grade 0—no evidence of ulcers or mucositis
Grade 1—erythema but no ulceration
Grade 2—1 or 2 small (<2 mm), single ulcers
Grade 3—1 large or 3 or more small ulcers
Grade 4—multiple large ulcers and/or involvement of 50% of pouch mucosal surface area The animals were evaluated both for the ability of TGF-α to delay the onset and reduce the severity of mucositis. The data presented here are based upon clinical observations. Histologic evaluation of biopsied cheek pouches corroborated these observations.

The mucositis grades were averaged for all four groups over an 18 day period and it was found that groups receiving TGF-α had lower overall scores thus establishing that TGF-α reduced the severity of mucositis. The best results were obtained with Group III, the low dose group. The data for days 0-12 are presented in FIG. 1. From day 12 through day 18, mucositis in all groups was resolved.

Figure 2:
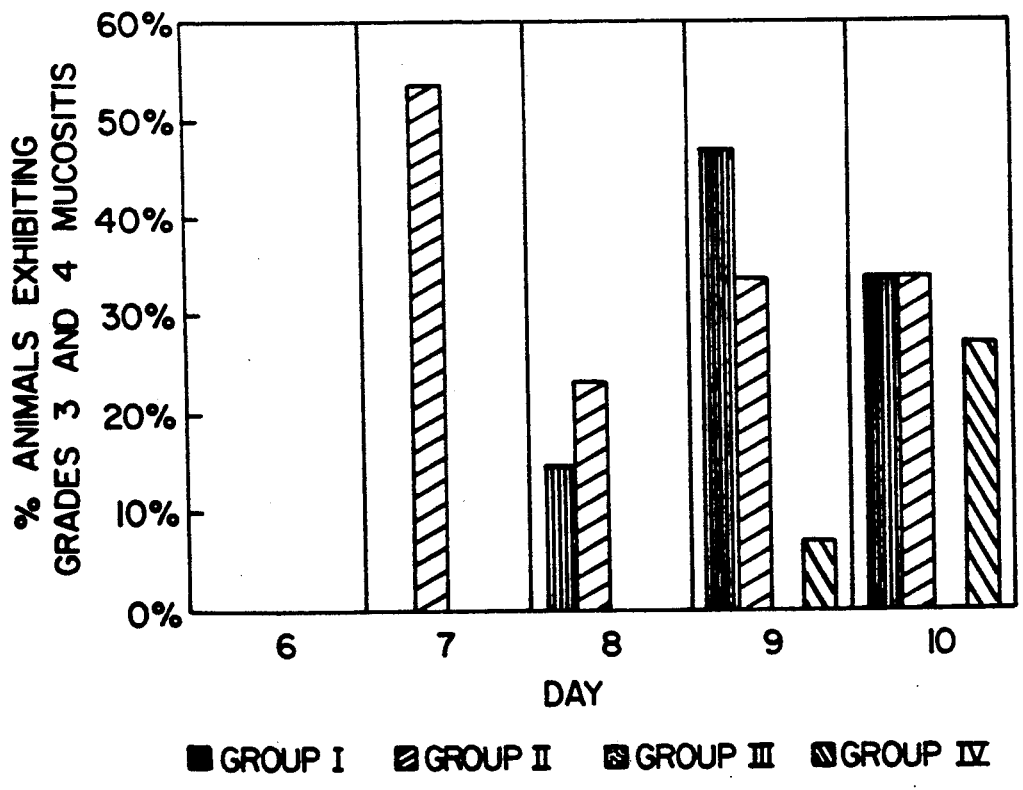
FIG. 2 illustrates the number of animals exhibiting severe oral mucositis from days 6 through 10.

The development of grade 3 and 4 mucositis was determined over several days and it was found that TGF-α delayed the onset of mucositis. This is indicated by the data presented in FIG. 2. The animals in Group IV did not develop grade ¾ mucositis until day 9. For animals in Group III, grade ¾ mucositis did not develop. In contrast, grade ¾ mucositis developed at day 7 for Group II and day 8 for Group I.

We claim:

1. A method of preventing chemotherapy or radiotherapy induced oral mucositis in a mammal which comprises administering an effective dose of a growth factor which is a polypeptide of the formula:

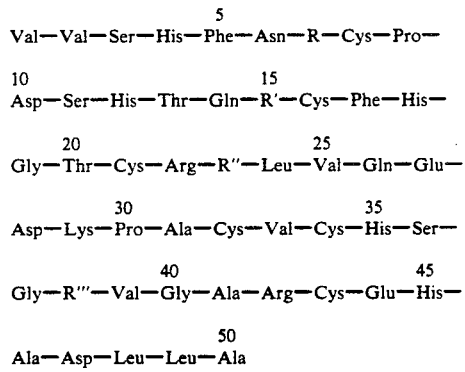

wherein R is Asp or Lys, R' is Phe or Tyr, R" is Ser or Phe and R'" is Phe or Tyr, to said mammal prior to or during said chemotherapy or radiotherapy.

2. The method of claim 1 wherein R is Asp, R' is Phe, R" is Phe and R'" is Tyr.

3. The method of claim 2 wherein said growth factor is combined with another growth factor.

4. A method of treating chemotherapy or radiotherapy induced oral mucositis in a mammal which comprises administering an effective dose of a growth factor which is a polypeptide of the formula:

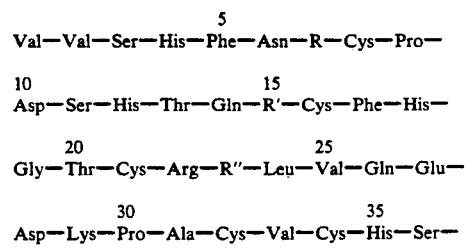

-continued

Gly—R'''—Val—Gly—Ala—Arg—Cys—Glu—His—
 40 45

Ala—Asp—Leu—Leu—Ala
 50 wherein R is Asp or Lys, R' is Phe or Tyr, R'' is Ser or Phe and R''' is Phe or Tyr, to said mammal.

5. The method of claim 4 wherein R is Asp, R' is Phe, R'' is Phe and R''' is Tyr.

6. The method of claim 5 wherein said growth factor is combined with another growth factor.

7. The method of claim 1 wherein said effective dose is within the range of about 0.01–100 μg/dose, administered 2–4 times daily, of said growth factor, alone, or in combination with other growth factors.

8. The method of claim 7 wherein said dose is within the range of about 0.1–50 μg/dose.

9. The method of claim 4 wherein said effective dose is within the range of about 0.01–100 μg/dose administered 2–4 times daily, of said growth factor, alone, or in combination with other growth factors.

10. The method of claim 9 wherein said dose is within the range of about 0.1–50 μg/dose.

* * * * *